United States Patent [19]
Sonoi et al.

[11] 4,452,889
[45] Jun. 5, 1984

[54] METHOD OF PRODUCING INOSINE AND/OR GUANOSINE

[75] Inventors: Koji Sonoi, Suita; Yasuhiro Sumino, Kobe; Muneharu Doi, Takarazuka, all of Japan

[73] Assignee: Takeda Chemical Industries, Ltd., Osaka, Japan

[21] Appl. No.: 389,459

[22] Filed: Jun. 17, 1982

[30] Foreign Application Priority Data

Jun. 22, 1981 [JP] Japan .................................. 56-97310

[51] Int. Cl.³ ........................ C12N 1/00; C12P 19/40; C12R 1/07; C12R 1/125; C12R 1/13; C12R 1/15
[52] U.S. Cl. ...................................... 435/88; 435/243; 435/813; 435/832; 435/839; 435/840; 435/843
[58] Field of Search ...................... 435/87, 88, 91, 92, 435/243, 244, 253, 802, 813, 832, 839, 840, 843

[56] References Cited

U.S. PATENT DOCUMENTS 3,625,825 12/1971 Shibai et al. ........................ 435/88

FOREIGN PATENT DOCUMENTS 53-3580 1/1978 Japan .................................. 435/813

OTHER PUBLICATIONS

Kotani et al., Agric. Biol. Chem., 42(2) 399–405 (1978).

Primary Examiner—Esther M. Kepplinger
Attorney, Agent, or Firm—Wenderoth, Lind & Ponack

[57] ABSTRACT

A method of producing inosine and/or guanosine comprising cultivating a microorganism in a medium containing a carbohydrate, in which method a carbohydrate is added either continuously or intermittently to the medium when and in the state that the concentration of the carbohydrate in the medium is less than about 1 percent so that the carbohydrate concentration of the medium is maintained below about 1 percent.

5 Claims, No Drawings

METHOD OF PRODUCING INOSINE AND/OR GUANOSINE

This invention relates to a method of producing inosine and guanosine.

Inosine and guanosine are important starting materials for the synthetic production of pharmacologically active compounds and flavorant 5'-ribonucleotides, and it is of great commercial importance to produce these starting material compounds at low cost and on a large scale.

There have been known several methods for the production of inosine and/or guanosine, one of which comprises extracting these compounds from naturally-occurring materials, while another is a fermentation process comprising the use of a microorganism. However, these methods have several drawbacks, e.g. several complicated series of production steps, use of expensive raw materials or low fermentation yield, and are not necessarily satisfactory from industrial points of view.

The present inventors explored possibilities for the establishment of an industrial process for producing inosine and/or guanosine by means of a microorganism in a high fermentation yield and found that if the carbohydrate as a main medium component is not added en bloc as is conventionally practiced, but is added either intermittently or continuously in small installments in the course of cultivation with reference to the monitored consumption of the carbohydrate by the microorganism, the production of inosine and/or guanosine is remarkably increased. This invention has been conceived and developed on the basis of this finding.

This invention relates to a method of producing inosine and/or guanosine comprising cultivating an inosine- and/or guanosine-producing strain of microorganism in a culture medium containing a carbon source carbohydrate, and harvesting inosine and/or guanosine from the resulting fermentation broth, characterized in that a carbohydrate is added either intermittently or continuously to the culture medium when and in the state that the concentration of the carbon source carbohydrate in said medium is not higher than about 1 percent, in such a manner that the carbohydrate concentration of the medium is maintained at a level not exceeding about 1 percent.

As examples of the carbohydrate as a carbon source according to this invention, there may be mentioned sugars [e.g. glucose, fructose, mannose, sucrose, maltose, molasses, starch, starch hydrolysate (e.g. corn starch saccharification liquor), etc.], sugar alcohols (e.g. sorbitol), and so on.

In the method of this invention, a carbohydrate as a carbon source is added either intermittently or continuously so as to maintain the carbohydrate concentration of the medium at a level not exceeding about 1%. The concentration of the carbon source carbohydrate in the medium at initiation of cultivation may be either less or more than about 1%. In the latter case, however, the addition of the carbohydrate should be started after the carbohydrate level has dropped to about 1% or less with the progress of cultivation. It should be noticed that the feed concentration of the carbohydrate in the starting medium is preferably not higher than about 4 percent.

As mentioned above, the carbohydrate concentration of the medium is controlled at a level not exceeding about 1% in the method of this invention. However, the period during which the carbohydrate concentration is so controlled need not be the entire cultivation time but may be a certain limited period, for example the period from the 12th hour or thereabouts after initiation of cultivation down to the end of the cultivation time, in which period the production of inosine and/or guanosine is maximal.

In order to control the carbohydrate concentration of the medium at a predetermined level, the residual amount of carbohydrate in the medium must be constantly known. For this purpose, the carbohydrate concentration in the medium may be directly monitored using a conventional carbohydrate assay reagent, or indirectly determined by measuring the concentration of oxygen or carbon dioxide gas in the medium or effluent gas with a sensor means. The latter method, where the carbohydrate concentration in the medium is determined using a sensor is more convenient, for the carbohydrate concentration can be automatically controlled at a given level by associating the sensor instrument with the carbohydrate feeding device.

The microorganism employed for the purposes of this invention may be any species and strain of microorganism that is able to elaborate inosine and/or guanosine. Among specific examples of such microorganism are species of the genus Bacillus, the genus Brevibacterium, and the genus Corynebacterium.

Thus, *Bacillus pumilus* and *Bacillus subtilis* may be mentioned as examples of Bacillus species. More particularly, *Bacillus pumilus* No. 158-A-17 and *Bacillus subtilis* ATCC 13956 may be used.

*Bacillus pumilus* No. 158-A-17 has been deposited since June 4, 1981 at Fermentation Research Institute, Agency of Industrial Science and Technology, Ministry of International Trade and Industry, Japan (FRI) under the accession number of FERM BP-7 in accordance with the provision of the Budapest Treaty, and deposited since Jan. 11, 1967 at the Institute for Fermentation, Osaka (IFO), Japan under the accession number of IFO 12477. *Bacillus subtilis* ATCC 13956 has also been deposited since May 27, 1981 at IFO under the accession number 14124. The ATCC number referred to above is the accession number at the American Type Culture Collection (U.S.A.). The above IFO 12477 strain is mentioned in Japanese Patent Publication (examined) No. 46839/1976. The ATCC 13956 strain is listed in the The American Type Culture Collection Catalogue of Strains I, Fourteenth Edition, 1980.

As exemplary strains of the genus Brevibacterium, there may be mentioned *Brevibacterium ammoniagenes* ATCC 21477, ATCC 21478, ATCC 21479 and ATCC 21480 (all listed in the ATCC Catalogue of Strains, Fourteenth Edition, 1980).

In addition to the carbon source or sources, there are incorporated in the medium various nitrogen sources and other components in the conventional manner. The nitrogen sources may be organic nitrogenous materials such as corn steep liquor, cottonseed cake, yeast extract, dried yeast, fish meal, meat extract, peptone, casamino acid, etc., inorganic nitrogenous compounds such as ammonia gas, aqueous ammonia, ammonium sulfate, ammonium chloride, ammonium carbonate, ammonium nitrate, ammonium phosphate, etc. and organic nitrogen compounds such as urea, amino acids etc. In addition to the carbon and nitrogen sources mentioned above, suitable amounts of other substances such as various metals, vitamins, amino acids, etc.

which are necessary for growth of the microorganism and the accumulation of inosine and/or guanosine are also incorporated in the medium.

The cultivation is conducted under aerobic conditions, e.g. under shaking or aerated submerged culture conditions. The incubation temperature is generally selected from the range of about 20° C. to 45° C. and should be favorable to growth and multiplication of the microorganism and to the accumulation of inosine and/or guanosine. The pH of the medium is desirably within the range of about 5 to 9. To control the pH of the medium within this range, there may be added sulfuric acid, hydrochloric acid, ammonia gas, aqueous ammonia, aqueous sodium hydroxide, aqueous potassium hydroxide, calcium carbonate, calcium oxide or the like. When the microorganism is cultivated under such conditions for about 48 to 120 hours, generally a large amount of inosine and/or guanosine is accumulated in the medium.

The inosine and/or guanosine thus accumulated in the medium can be easily isolated by a conventional purification procedure such as ion exchange resin or activated carbon chromatography, precipitation, solvent extraction, etc.

There are several reports on the fermentative production of inosine and/or guanosine by means of microorganisms, but in these processes the entire amount of the main carbon source carbohydrate is invariably added en bloc to the medium before initiation of cultivation. [For example, Nogami et al: Amino Acids & Nucleic Acids 17, 66, 1967, Jho et al: Amino acids and Nucleic Acids 16, 100, 1967]

It has also been attempted, for the production of certain nucleic acid related compounds by way of fermentation, to add a supplemental amount of carbohydrates in the course of cultivation so as to increase the carbohydrate intake. [For example, Kotani et al: Agric. Biol. Chem. 42, 399, 1978]. The procedure is, however, intended to avoid such events as a deviation of the carbohydrate level of the medium from the normal concentration range and a consequent suppression of growth of the microorganism, and is definitely not intended to control the carbohydrate concentration of the medium at a given level.

In contrast, the method of this invention is such that an inosine and/or guanosine-producing microorganism is cultivated in a medium with the carbohydrate concentration thereof being controlled to a predetermined level of about 1 percent at the maximum in the course of elaboration of inosine and/or guanosine.

Thus, the method of this invention is a novel method which is quite distinct from the known methods referred to above, and is capable of providing an improved yield of inosine and/or guanosine relative to the carbohydrate consumed.

Since the method of this invention thus enables one to increase the yield of the fermentation product or products relative to the consumption of carbohydrates, it is made possible thereby to reduce the consumption of raw material carbohydrates. Thus, this invention provides an industrially useful production technology.

The following examples are further illustrative of this invention. It should be understood that in the examples all percents (%) are weight/volume percents (w/v %) unless otherwise specified.

EXAMPLE 1

A sterilized seed culture medium containing 2% sorbitol, 0.1% $KH_2PO_4$, 0.3% $K_2HPO_4$ and 2% dried yeast was inoculated with *Bacillus pumilus* No. 158-A-17 (FERM BP-7, IFO 12477) as picked from a nutrient agar plate and the inoculated medium was incubated under shaking at 37° C. for 18 hours. Then, a jar fermenter of 5-liter capacity was charged with 2 l of a sterilized production medium containing 0.8% glucose, 0.4% $(NH_4)_2SO_4$, 0.5% sodium glutamate, 0.05% $KH_2PO_4$, 0.1% KCl, 0.2% $CaCl_2.2H_2O$, 0.003% $MnSO_4.4H_2O$, 0.03% histidine, 200 μg/l biotin, 0.2% $MgSO_4.7H_2O$, 0.25% ribonucleic acid (purity 70.3%) and 1% corn steep liquor, and 200 ml of the seed culture prepared as above was transferred to this production medium in the jar fermenter. The cultivation was started at a temperature of 38° C. and a rotational speed of 1000 r.p.m. with an aeration rate of 1.2 l/min. During the cultivation period, 25% (v/v) aqueous ammonia was automatically introduced into the fermenter to maintain the medium at pH 6.4. The glucose solution as a carbon source was added in the following manner.

Method A:

Starting at the 9th hour after initiation of cultivation when the concentration of glucose in the medium had decreased to a level below 0.1%, a sterilized 80% solution of glucose was continuously added, with the concentration of glucose in the medium being monitored enzymatically using glucose oxidase at 2-hour intervals, so that the glucose concentration would be maintained within the range of 0.005% to 0.1%. The cultivation was thus conducted for 56 hours. The amount of glucose consumed during this time period was 160 grams.

Method B:

In the same manner as Method A, glucose was continuously added so as to maintain the glucose concentration of the medium at a level not exceeding 1%. The cultivation was thus conducted for 48 hours. The amount of glucose consumed during this period was 150 grams.

Method C:

As in Method A, glucose was continuously added from initiation of cultivation so as to maintain the glucose concentration of the medium within the range of 1.8% to 2.2%. The cultivation was thus conducted for 40 hours. The amount of glucose thus consumed was 140 grams.

Method D:

140 Grams of glucose was added at initiation of cultivation and the cultivation was continued for 42 hours, by the end of which time the glucose was completely consumed.

The amounts of inosine and guanosine obtained by the above various cultivation methods were determined by high performance liquid chromatography. The results, are shown in Table 1.

TABLE 1

|  | Method of adding glucose | *Combined yield of inosine and guanosine (g/l) | Percent yield, based on carbohydrate |
|---|---|---|---|
| Example 1-1 | Method A | 34.4 | 21.5 |
| Example 1-2 | Method B | 28.6 | 17.9 |

TABLE 1-continued

| | Method of adding glucose | *Combined yield of inosine and guanosine (g/l) | Percent yield, based on carbohydrate |
|---|---|---|---|
| Comparative Example 1-1 | Method C | 16.3 | 10.2 |
| Comparative Example 1-2 | Method D | 12.2 | 7.6 |

Note
*The combined yield values of inosine and guanosine in the Table are the values obtained by correcting the yield with the ratio of the liquid amount at the end of cultivation to the initial liquid amount.

EXAMPLE 2

Seed culture media of the same composition as that used in Example 1 were respectively inoculated with the strains indicated in Table 2 and incubated under shaking at 38° C. for 18 hours. Each of the resulting cultures was transferred to a production medium of the same composition as that of Example 1 and the cultivation was conducted in the same manner as Example 1. Glucose was added by Method A and Method D as described in Example 1. After the cultivation, the inosine and guanosine in each broth were assayed by the procedure mentioned in Example 1 and the yield relative to the carbohydrate consumed was calculated. The results are set forth in Table 2.

TABLE 2

| Strain | Method of adding glucose | Cultivation time (hrs.) | Percent yield, based on carbohydrate |
|---|---|---|---|
| Bacillus pumilus No. 158-A-17 (FERM BP-7, IFO 12477 | Method A Method D | 58 42 | 21.5 7.6 |
| Bacillus subtilis ATCC 13956 (IFO 14124) | Method A Method D | 64 48 | 17.3 12.0 |

EXAMPLE 3

A seed culture tank of 200-liter capacity was charged with 100 l of a seed culture medium of the same composition as that described in Example 1 and the medium was sterilized and cooled in the routine manner. The medium in the tank was then inoculated with a *Bacillus pumilus* No. 158-A-17 (FERM BP-7, IFO 12477) from a Sakaguchi flash and the cultivation was conducted at 37° C., 180 r.p.m. and 50 l/min. aeration. Separately, a fermentation tank of 2,000-liter capacity was charged with 900 l of a production medium similar to that of Example 1 except that 4% of corn starch saccharification liquor was added in lieu of 0.8% of glucose. After this production medium was sterilized and cooled in the conventional manner, 100 l of the aboveprepared seed culture was transferred to the medium and the cultivation was initiated at 38° C., 240 r.p.m. and 800 l/min. aeration. Starting from 20 hours after initiation of cultivation, corn starch saccharification liquor was intermittently added at intervals of 10 minutes, with the glucose concentration of the medium being monitored every hour by the glucostat method, so that the glucose concentration of the medium would be continued within the range of 0.001% to 0.1%. The cultivation was continued for 71 hours. During this period, 20%, based on the starting amount of the medium, of the saccharification liquor on a glucose basis was consumed. Throughout the incubation period, the pH of the medium was automatically adjusted to 6.3–6.5 with 25% aqueous ammonia. On completion of cultivation, the titers of inosine and guanosine in the broth were determined by high performance liquid chromatography. The titers were 29.6 g/l and 4.2 g/l, respectively. The combined yield of these two metabolites relative to the carbohydrate was 21.3%.

A 1,000-liter portion of the above fermentation broth was adjusted to pH 10 with sodium hydroxide and filtered. The filtrate (900 l) was passed through a column of Amberlite IRA-402 (Cl-form), an anion exchange resin (Rohm & Haas Co.), and elution was carried out with 0.2N-HCl at SV 1, whereby fractions containing inosine and/or guanosine (total: 4000 l) were obtained. These fractions were combined and adsorbed on a column packed with 850 l of activated carbon and elution was carried out with 5 v/v % butanol-water. The fractions containing inosine and/or guanosine (total: 5100 l) thus obtained were pooled, neutralized with sodium hydroxide and concentrated under reduced pressure (140 l). This concentrate was cooled to 5° C., whereby mixed crystals of inosine (22.0 kg) and guanosine (2.9 kg) were obtained.

What we claim is:

1. A method of producing inosine and/or guanosine comprising cultivating an inosine and/or guanosine-producing strain of microorganism in a medium containing a carbohydrate as a carbon source to cause the microorganism to elaborate and accumulate inosine and/or guanosine in the resulting fermentation broth, and harvesting the inosine and/or guanosine from the broth, wherein the carbohydrate concentration in the medium at the initiation of cultivation is not more than 1 percent or is more than 1 percent, and when it is more than 1 percent cultivation is carried out until the concentration is decreased to not more than 1 percent; a carbohydrate is added continuously or intermittently to the medium when the concentration of the carbohydrate in the medium is not more than about 1 percent; and the carbohydrate concentration of the medium is maintained at not more than about 1 percent after said addition.

2. A method according to claim 1, wherein the concentration of the carbohydrate in the medium at initiation of the cultivation is more than about 1 percent.

3. A method according to claim 1, wherein the concentration of the carbohydrate in the medium at initiation of the cultivation is not more than about 4 percent.

4. A method according to claim 1, wherein the carbohydrate is glucose and its concentration in the medium is maintained in the range of 0.005 to 0.1 percent.

5. A method according to claim 1, wherein the carbohydrate is corn starch saccharification liquor and its concentration in the medium is maintained in the range of 0.001 to 0.1 percent, on a glucose basis.

* * * * *